(12) United States Patent
Dorfman

(10) Patent No.: US 6,835,067 B2
(45) Date of Patent: Dec. 28, 2004

(54) PREFABRICATED DENTAL INLAY FORMS FOR USE IN FILLINGS

(76) Inventor: Jeffrey Dorfman, 18 E. 50th St.--PhC, New York City, NY (US) 10022

( * ) Notice: Subject to any disclaimer, the term of this patent is extended or adjusted under 35 U.S.C. 154(b) by 105 days.

(21) Appl. No.: 10/094,755

(22) Filed: Mar. 11, 2002

(65) Prior Publication Data

US 2003/0170593 A1 Sep. 11, 2003

(51) Int. Cl.[7] ................................................ A61C 5/04
(52) U.S. Cl. ...................................... 433/226; 433/218
(58) Field of Search ................................ 433/218, 219, 433/220, 221, 226

(56) References Cited

U.S. PATENT DOCUMENTS

| | | | | |
|---|---|---|---|---|
| 1,262,629 A | * | 4/1918 | Brouillet | 433/226 |
| 4,355,980 A | * | 10/1982 | Dwight | 433/226 |
| 4,993,951 A | * | 2/1991 | Schumacher | 433/226 |
| 5,358,406 A | * | 10/1994 | Bjerknes | 433/226 |
| 5,368,831 A | * | 11/1994 | Tanaka | 433/226 |
| 5,695,340 A | * | 12/1997 | Lee et al. | 433/226 |

* cited by examiner

*Primary Examiner*—Todd E. Manahan

(57) ABSTRACT

Chair-side, modifiable, dental inlay preforms of highly durable material are bonded within mainly posterior teeth following removal of decay. These inlay preforms offer increased strength and resilience over direct composites while being faster, less costly and easier to place than indirect inlays. A kit of preforms containing multiple bins of various geometrical shapes and sizes are available to repair mainly molars and premolars in the upper and lower arches. The inlay preforms can be modified with standard acrylic and/or porcelain burs and inserted with standard dental bonding material. A removable grip eases the try-in process.

5 Claims, 8 Drawing Sheets

PREFABRICATED DENTAL INLAY FORMS FOR USE IN FILLINGS

BACKGROUND OF THE INVENTION

Tooth-colored dental bonded fillings that are placed in cavity preparations following caries (cavity) removal are a popular alternative to traditional silver fillings. Patients prefer these cosmetically attractive restorations but the procedure is technically more difficult than that for silver fillings.

The technique for the placement of tooth-colored dental bonded fillings may be divided into two types: First, the direct technique wherein the filling is a light-cured or chemically-cured bonding material that is directly shaped in the cavity preparation and hardened in place right after caries removal. The material is usually an acrylic based polymer. Second, the indirect technique where at the first visit, the dentist removes the cavity and takes an impression (or mold) of the tooth. The patient leaves with a temporary filling. At the second visit the dentist inserts a custom-fabricated dental filling that is then sealed in place with a light-cured or chemically-cured bonding material. The fabricated filling material can be acrylic, porcelain or "ceromer", a hybrid of an acrylic and a ceramic powder filler.

In the direct technique, unlike traditional silver fillings that are inserted in a cavity preparation as a semi-solid mass, the bonding material is a viscous liquid, which can flow in unintended places and encapsulate voids that compromise the strength of the restoration. The bonding material, usually an acrylic, is light-cured or chemically cured to harden after placement.

Another difficult part of the procedure for dentists is making the dental bonding material contact the adjacent tooth. This is necessary to prevent subsequent food impaction should a contact be left open. The tendency of the semi-cured material to stick to any instrument used to manipulate it results in "tug back" from the bonding surface, especially when bonding to moist dentin. The difficulty in creating a smooth surface transition between the natural and restored surface can act to trap bacterial debris.

The insertion of tooth-colored dental bonded fillings into a clean cavity preparation in a tooth requires the "building up" of multiple layers, each with it's curing cycle and potential for the formation of a delaminated interface between layers from potential wet films on the surfaces. The hardened underlayers have fewer chemical bonding sites for the next layer to adhere to requiring physical abrasion for proper bonding. Each subsequent layer must be thoroughly hardened before its surface can be abraded.

Polymerization shrinkage, which occurs while curing the directly placed bonding material can result in the withdrawal of the bonding compound from the walls of the cavity and causes tensile stresses between the bonded surfaces that compromise the life of the restoration.

In the indirect technique, a dental filling material is hardened in a dental laboratory using heat and pressure during curing. This has superior mechanical properties to one directly placed and hardened in a tooth. The customized, indirectly fabricated dental restoration is stronger and more wear resistant but it takes two visits and more of the dentist's time. This is significantly more expensive and more inconvenient to the patient. It is also more expensive because of the cost of custom fabrication of the restoration by a dental laboratory. Furthermore, a tooth can become increasingly sensitive each time it is worked on and this technique requires at least two interventions and sometimes more if the custom filling does not fit. This disclosure involves a hybrid of the two techniques.

Copy milling or CAD-CAM milling (Computer Aided Design-Computer Aided Manufacturing) of blocks of ceramics or composites can produce indirect inlays and onlays chair side. One well-known Cad-Cam machine is made by Cerec (Siemens, Germany). This machine scans an optical impression of the tooth preparation following caries removal and mills an inlay or onlay out of a block of ceramic or composite in only a few minutes. The disadvantages of this technique include the need for significant training and the inaccuracy of the fit of the inlay or onlay. Currently, these machines cost $90,000 to purchase plus $40 for each ceramic blank, which makes it very expensive for patients. In contrast, prefabricated dental inlay preforms are intuitive to use and don't require any special machinery so the cost per use would only be a few dollars at most. The accuracy of the fit of the preforms, like Cerec, will not match that provided by a custom lab fabricated dental inlay or onlay, but it will be a lot faster, more convenient and less invasive to the tooth. It will also be a lot stronger than the direct technique. Unlike Cerec and custom inlays or onlays, it will be very cost-effective for patients.

The Invention

A method is described to help dentists overcome these difficulties with the use of prefabricated, geometrically shaped, inlay preforms of various sizes with approximately trapezoidal, rectangular and square faces. The cavity preparation of a tooth is roughly one of these shapes. It is possible for a dentist to choose from assorted sizes of prefabricated, geometrically shaped dental inlay preforms to see which one might most ideally fill in the tooth. Minor misfits could be removed with a dental drill on internal surfaces. The practitioner would place the chosen piece, or pieces, into the space of the cavity preparation after first placing a layer of chemically cured, flowable bonding material. This latter material, that is not a unique part of this disclosure, would function in a manner similar to cement encompassing a floor tile. The end result is a restored tooth with a smooth, continuous exterior almost indistinguishable in appearance and strength from the original tooth.

The prefabricated dental inlay preforms are made in laboratory conditions using heat and pressure during curing to provide superior mechanical properties. The applicant's preforms could be manufactured using thermally cross-linked acrylic polymers, tough ceramic porcelains or hybrid "ceromers". Kits of prefabricated shapes of enough variety to anticipate any needed restoration are contemplated by this invention. Minor chair-side modifications will tailor the prefab shape to the individual tooth. The occlusal and proximal surfaces can be finished to match the adjoining teeth. Applicant's preforms can be equipped with sidewall grooves to offer an interlocking means or roughened or sand blasted surface to add more bonding sites. This insures that these preformed, polymerized inserts have better mechanical bonding characteristics. Small spacing bumps, hemispheres or conic projections, molded onto the bonding surfaces of the preforms will space the preform a known distance from the surfaces of the cavity excavation to insure an adequate thickness of bonding compound within the bonding interface.

Applicant's invention provides patients with the strength of an indirectly fabricated tooth-colored filling that is placed with the one-visit convenience and cost savings of a direct filling. There will be less wear on the biting surface of a restoration manufactured extra-orally under controlled pressure and temperature. Since the bulk of the filling will already be completely polymerized during manufacture there will be much less shrinkage during the insertion and hardening of the filling in the tooth. The use of a preform results in a finer gap junction with a smaller bonding interface inducing less of the shrinkage stresses, maintaining the hybrid adhesive junction between the sealed surfaces and decreasing the potential for microleakage.

Applicant envisions a few dozen shapes mainly in the molar and premolar sizes for the upper and lower arch of teeth. Various colors of the preform could also be offered. For simplicity it is thought to initially offer a shade comparable to A2 on the Lumin (Tm) scale. A small tab or handle temporarily attached to the biting surface of the preform will ease its manipulation when trying it in or finish-cutting it. This can be cut away after setting in place or just prior to final bonding.

Though hybrid technologies are used to form full veneer temporary crowns, none have been considered for cavity filling preforms envisioned by the applicant. The shapes contemplated are singly or in combination used to fill the typical void formed in decay removal in the intracoronal and proximal areas of mainly molars and premolars. The inlay perform shapes will closely match the standard cavity preparation classification system as described in Sturdevant's "The Art and Science of Operative Dentistry, Fourth Edition. Copyright 2002." These Classes are labeled with Roman numerals I through V. Class I is a repair to the occlusal surface alone. Class II involves two or more tooth surfaces in molars and premolars, such as the mesioocclusal (MO) or the distoocclusal (DO) surface. Reconstruction to three surfaces in the mesioocclusodistal (MOD) is considered repairable by all the methods discussed. Repairs involving the complete replacement of a portion of the crown of the tooth including at least one cusp are considered to be partial onlays and not defined as an inlay for the purpose of this invention. Complete crown replacement is beyond the techniques described in this application. Other classes involving repairs to facioocclusal and linguooclusal excavations. Partial anterior tooth surfaces also can be within the scope of this invention.

There are several commercial advantages to this invention. This invention incorporates the strength of a prefabricated dental inlay shape with the efficiency of a direct bonded filling. A stronger filling can be placed in teeth than that obtained with the most commonly used direct bonding technique. This indirectly fabricated inlay could be placed into a tooth in one visit, instead of two, saving the patient a lot of time and substantially reducing the likelihood of a root canal flare-up. This procedure could be priced more like that of a typical direct bonded filling since it only requires one visit and there is no additional laboratory fee associated with custom fabrication. It could dramatically alter the way restorative dentistry is practiced.

DETAILED DESCRIPTION OF THE DRAWINGS

Figure 1:
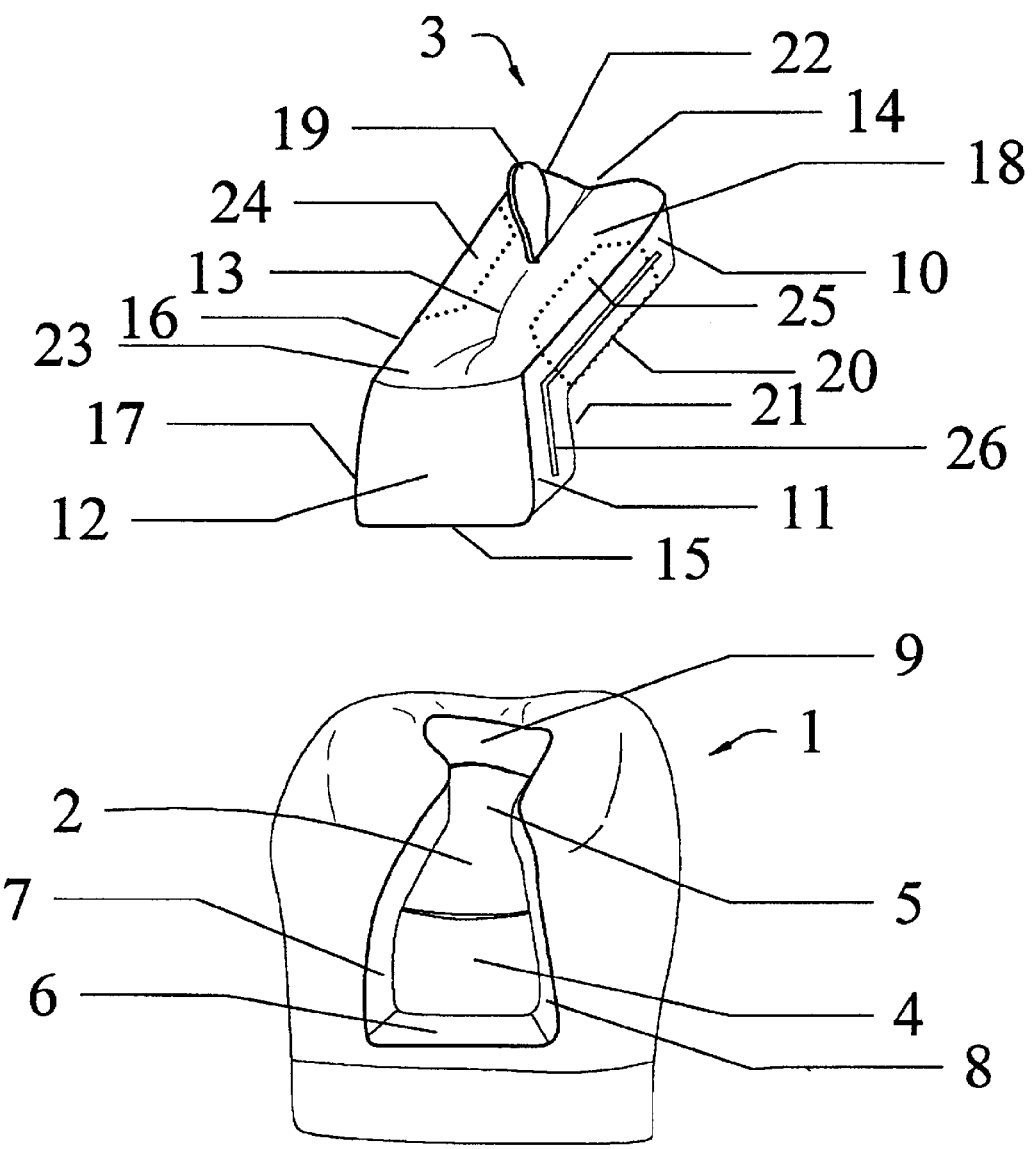
FIG. 1 is an exploded, perspective view of a typical Class II mesioocclusal (MO) cavity with matching preform showing portions removable at chair-side.

FIG. 1 shows an exploded perspective view of a molar or premolar 1 with a prepared cavity 2 with a typical mesioocclusal preform 3. The cavity has an axial wall 4, a pulpal floor 5, a gingival wall 6, facial wall 7, lingual wall 8 and a distal wall 9. The preform 3 is manufactured with modifiable surfaces that correspond to those formed by the cavity. The preform has a lingual surface 10 with lingual descender surface 11, gingival surface 15, proximal surface 12, facial surface 16, with facial descender surface 17. Additional surfaces are distal surface 14, pulpal surface 20 and axial surface 21. The occlusal surface 18 has a rudimentary groove 13, which is then shaped with typical dental instruments to match the surface of the opposing tooth in centric occlusion. Cusps 22 and 23 are manufactured with enough material to allow the practitioner to remove material to mate with the occlusal surface of the tooth. A small tab or handle 19 is provided by the manufacturer to ease the trying-in and modification process. This tab is cut away after the preform is bonded in place. Though the tab is shown protruding from a portion of the occlusal surface, other placements are equally feasible. Lateral groove 26 aids in retaining the preform within the bonding matrix material used to seat and cement the preform within the tooth cavity preparation. The preform 3 is modified at chair-side to remove materials in regions 24 and 25 to fit the excavated cavity preparation 2 in the molar 1.

Figure 2:
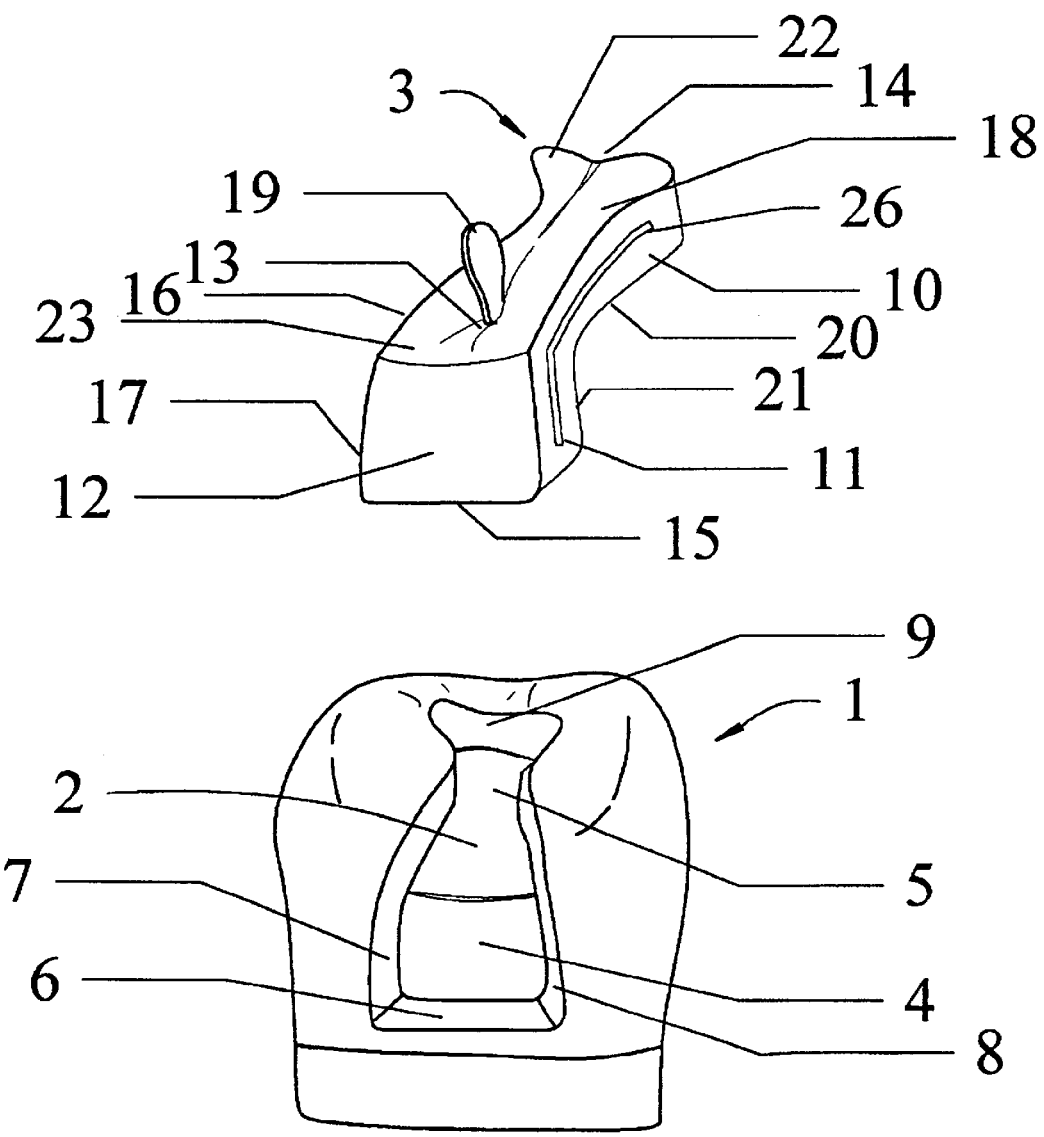
FIG. 2 shows an exploded, perspective view of a modified Class II mesioocclusal (MO) preform insert, after chair-side modification, useful for a mesioocclusal repair.

FIG. 2 shows the preform 3 modified to fit within the mesiooclussal (MO) cavity 2. Groove 26 can extend around the mating surfaces that abut the walls 6, 7, 8 and 9 of the cavity. Preform surfaces 20 and 21 can be equipped with tiny bumps or projections (shown in FIG. 8) to act as spacing elements to support the preform a known distance above the mating pulpal floor and axial wall to insure an adequate bonding agent interface thickness. In this manner, the bonding interface cannot be "starved" by having too much of the bonding compound squeezed out of the mating interface.

Figure 3:
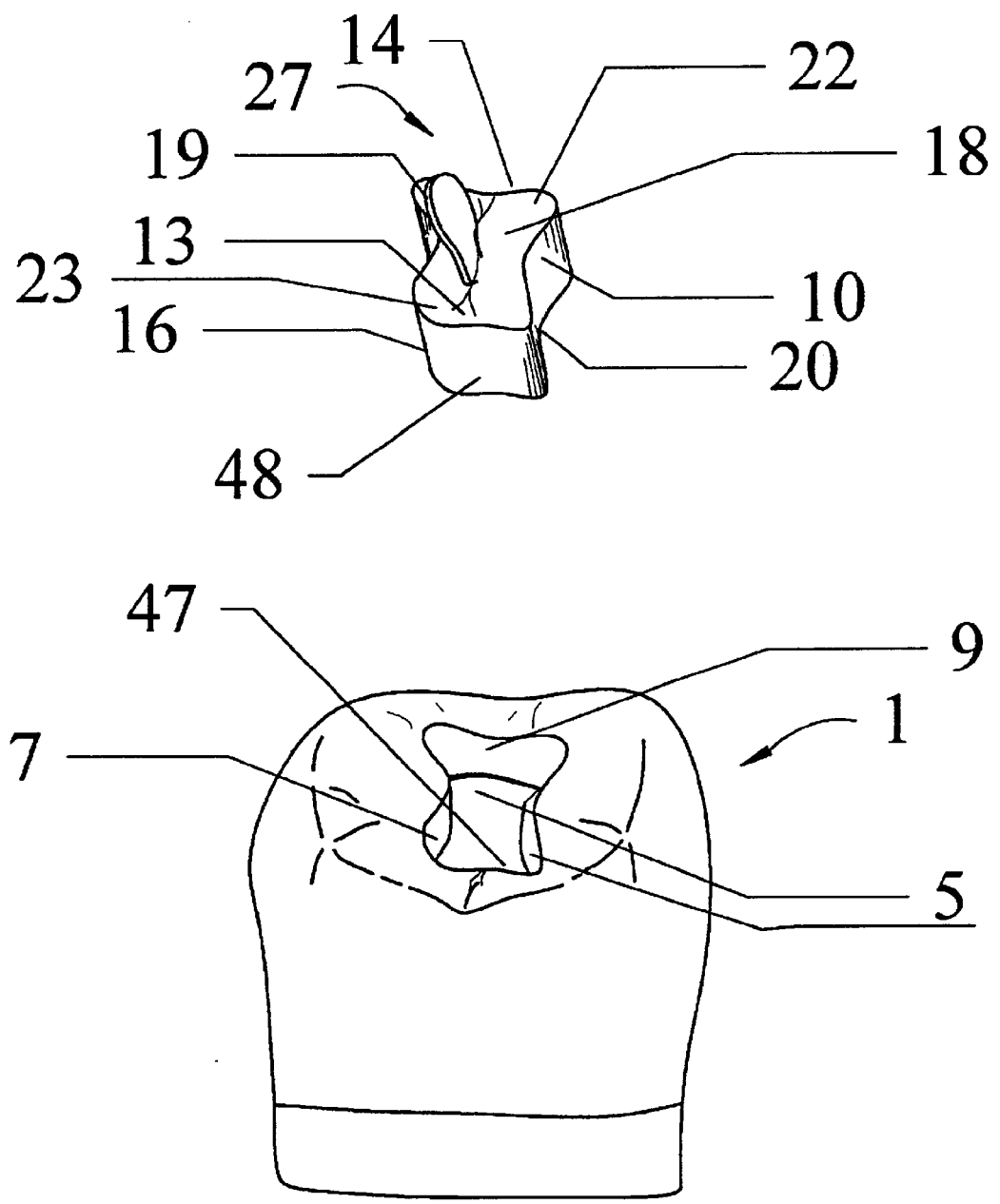
FIG. 3 shows an exploded, perspective view of a Class I preform insert useful for an occlusal surface repair.

FIG. 3 shows an exploded view of an occlusal preform 27 with a removable try-in tab 19 having an occlusal surface 18 with partial cusps 22 and 23. Lingual surface 10 of the preform mates with lingual wall 8 of the cavity, forming a bonding interface. Similar bonding interfaces are formed between facial surface 16 and facial wall 7, distal surface 14 and distal wall 9, mesial surface 48 and mesial wall 47 and between pulpal surface 20 of the preform and pulpal floor 5 of the tooth. Preliminary groove 13 can be modified to mate in centric occlusion with the matching tooth of the opposing arch after the bonding compound has set.

Figure 4:
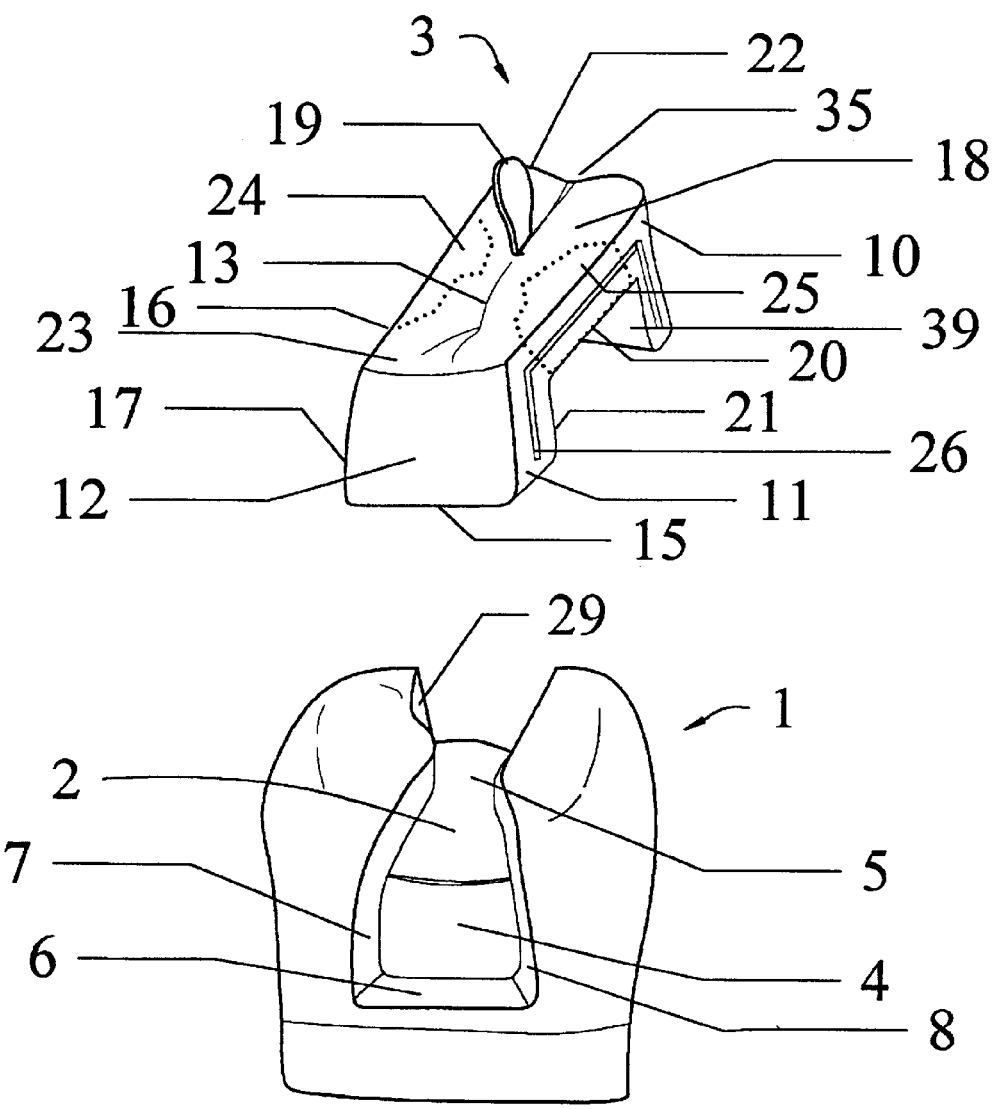
FIG. 4 shows an exploded, perspective view of a Class II (MOD) preform with two proximal descenders useful for a MOD repair.

FIG. 4 details an exploded perspective view of a mesioocclusodistal (MOD) preform 3 and a prepared tooth 1 viewed from the mesial side. The tooth is milled with rotary cutters and burs to form a cavity preparation 2 with pulpal floor surface 5, facial wall 7, lingual wall 8, gingival wall 6 on the mesial side and distal gingival wall 36 (best viewed in FIG.

6) on the distal side. The modifiable preform 3 is provided with roughly matching surfaces that can be machined at the chair-side to fit the cavity preparation 2. The preform 3 has a proximomesial side 12, a proximodistal side 35 and an occlusal surface 18 having representative partial cusps 22 and 23 and groove 13. Facial surface 16 mates with facial wall 7 after modification by removing volume 24. Likewise, lingual surface 10 mates with lingual wall 8 after removal of volume 25. Mesiogingival surface 15 mates with mesiogingival wall 6. Lingual surface 10 is shown with a typical mesial descender 11 and a distal descender 39. Groove 26 in the lingual surface 10 and in facial surface 16 (not shown) act to mechanically lock the preform into the prepared tooth when embedded in the composite compound used to cement the preform in place. A try-in tab 19 that can be gripped by a forceps, hemostat or other holding tool is shown protruding from the occlusal surface and can be cut away after cementing the preform in place.

Figure 5:
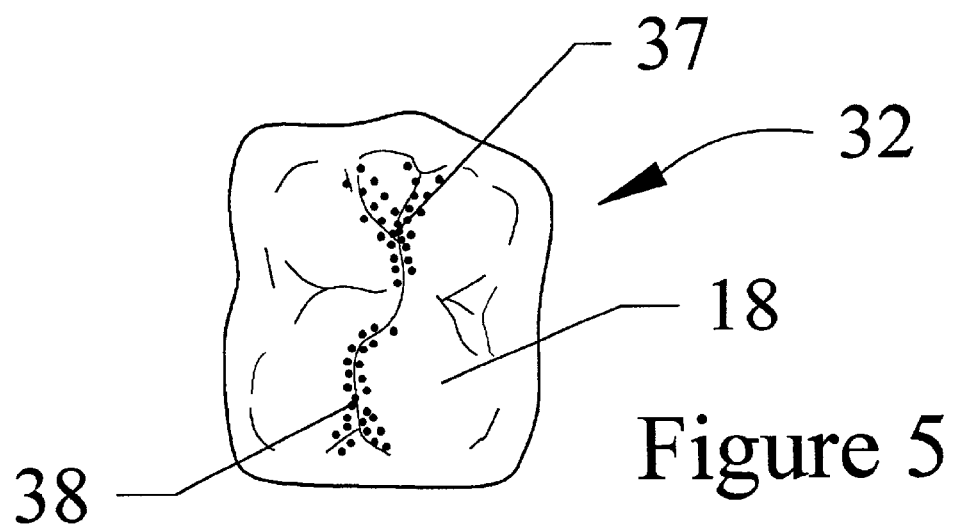
FIG. 5 is a top plan view of the unmodified occlusal surface of a typical molar with caries.
Figure 6:
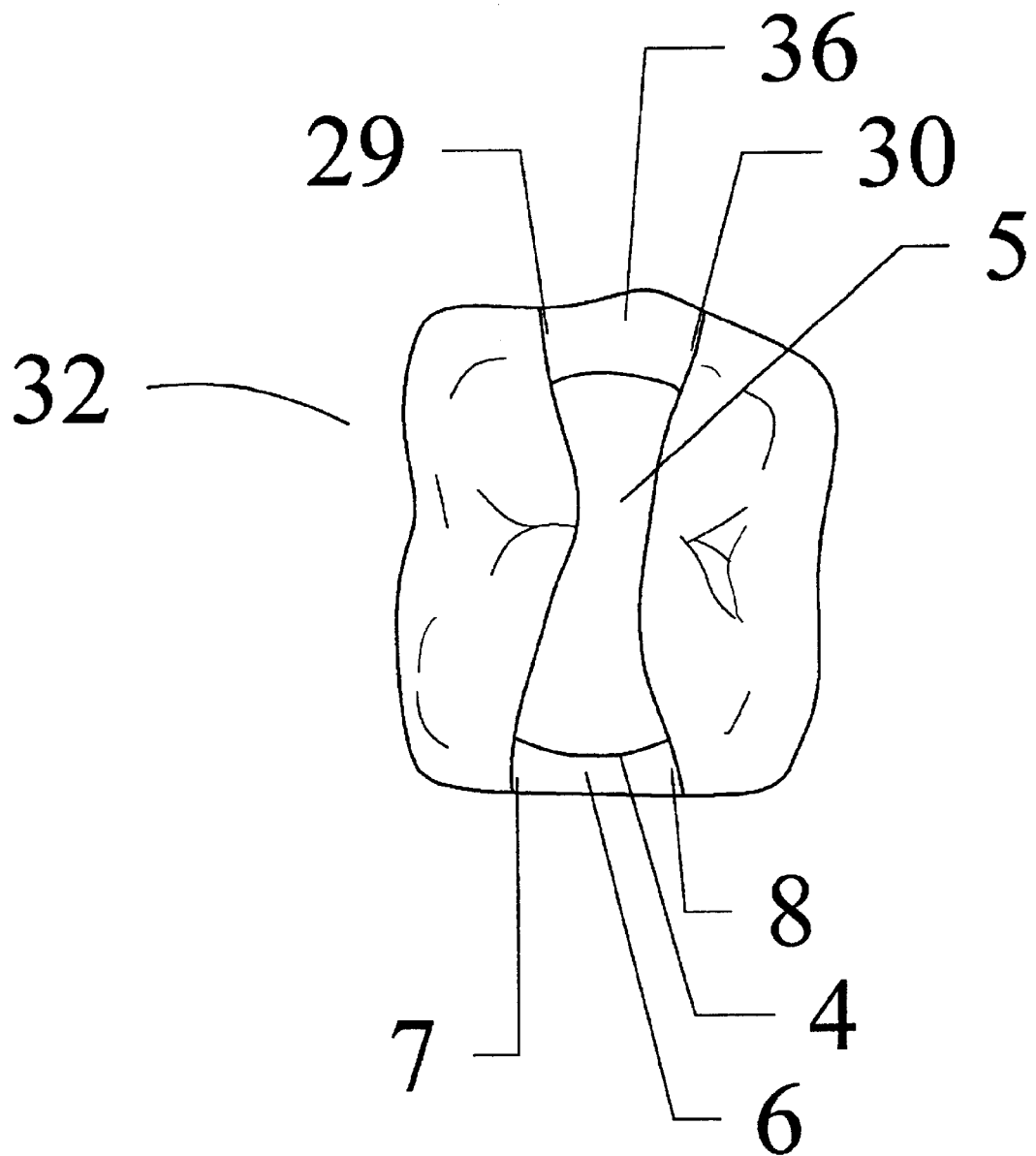
FIG. 6 is the same molar with the caries excavated showing the tooth preparation cavity formed.
Figure 7:
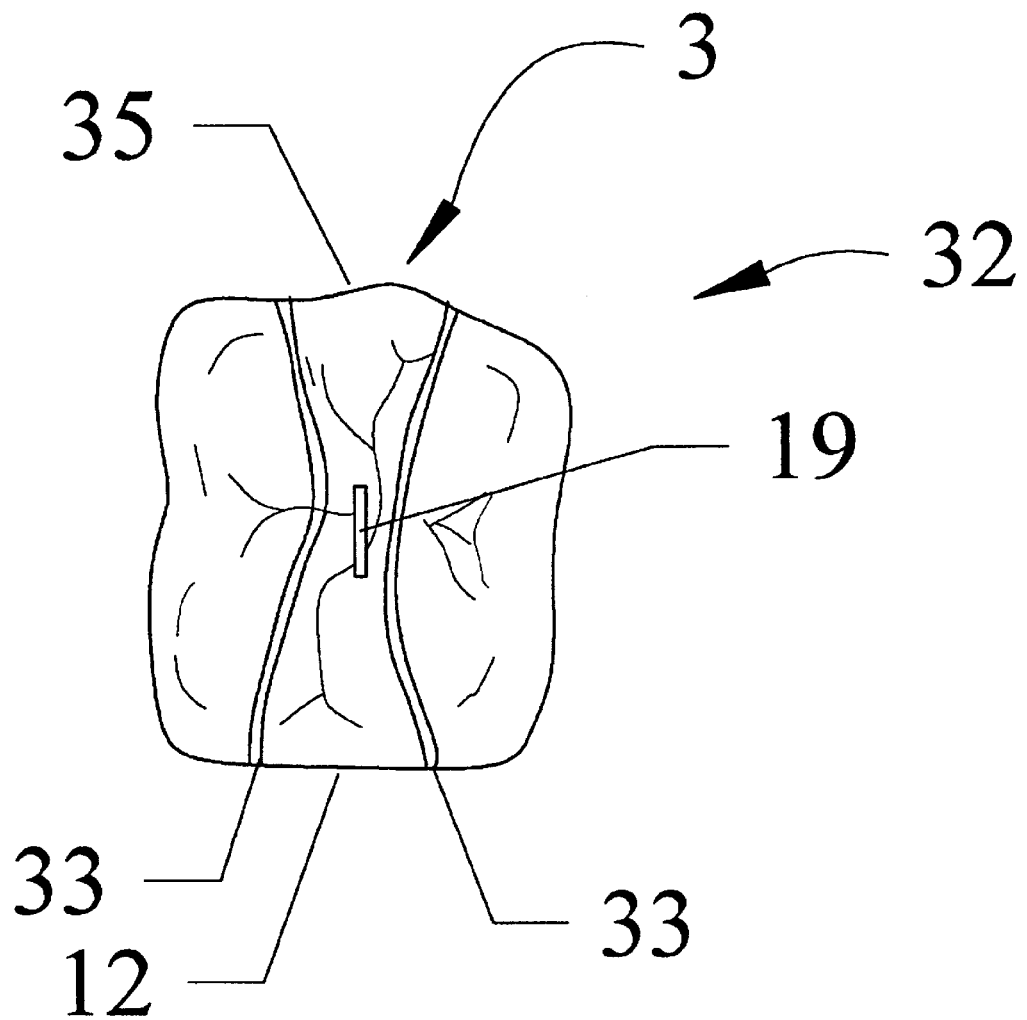
FIG. 7 shows the modified preform (MOD) placed in the same molar.

FIG. 5 shows a top view of a typical molar 32 with carious sections 37 and 38 in need of a MOD repair. FIG. 6 is the same molar with the carious sections removed. Visible are the pulpal floor 5, the mesiogingival wall 6 and the distogingival wall 36. The facial wall 7 and lingual wall 8 extend the length of the occlusal surface. FIG. 7 shows the same tooth 32 with the modified preform 3 in the try-in position. Try-in tab 19 is shown from the top. Mesioproximal surface 12 and distoproximal surface 35 are shown. Composite fill channels 33 retain the preform when the composite compound hardens.

Figure 8:
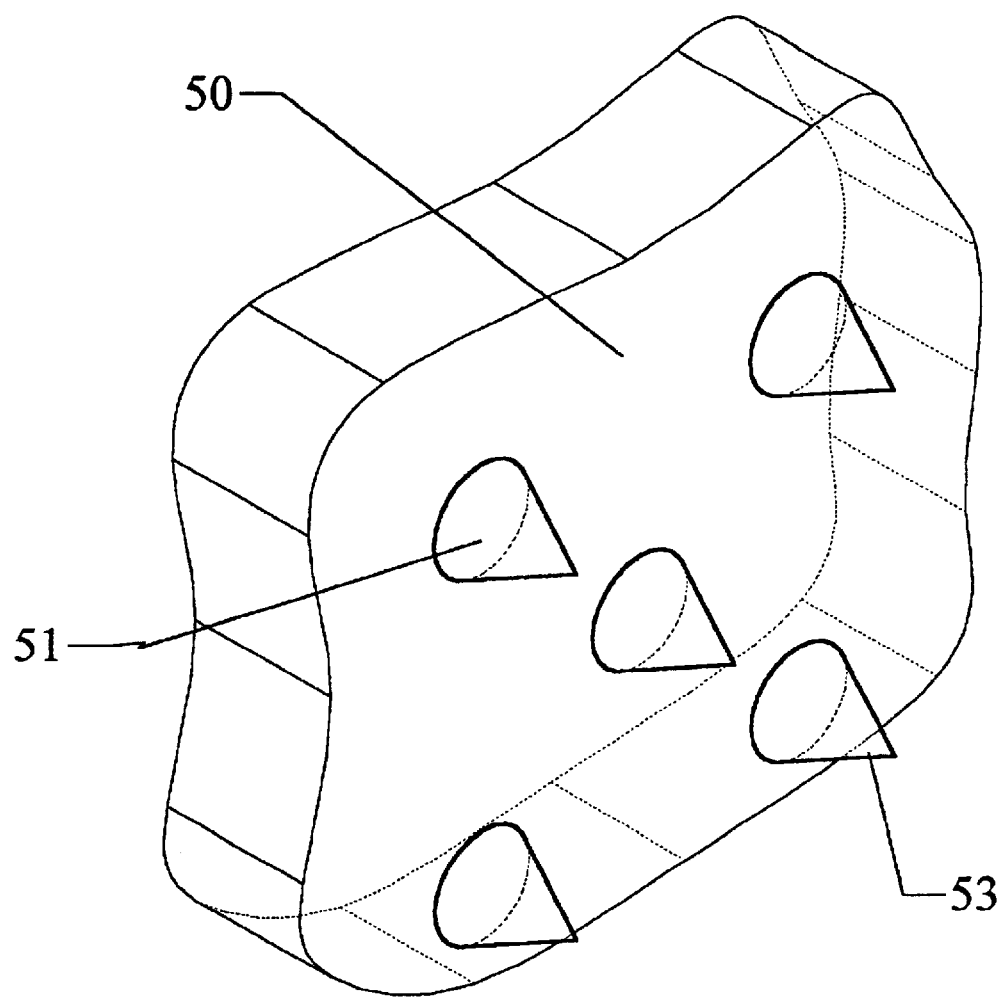
FIG. 8 shows a close up perspective view of surface bumps on bonding surfaces.

FIG. 8 shows a number of projecting bumps 51 molded onto the bonding surface 50 of a typical preform. Tips 53 of the projections touch the surface of the excavated cavity resulting in a bonding space of a thickness determined by the height of the projecting bumps 51. This minimum height guarantees a bonding interface with enough bonding compound to prevent starving the interface of necessary bonding material. These bonding bumps will be a fraction of a millimeter in height.

What is claimed is:

1. A dental apparatus comprising a kit of modifiable, durable, shaped solids used to restore mainly premolar and molar defects in one chairside sitting having at least one manufactured preform insert having an occlusal surface with included fossae, a lingual surface for bonding, a facial surface for bonding, a distal surface for bonding, a mesial surface for bonding, and a pulpal floor surface for bonding having surface bumps an said pulpal floor surface, to property space said shaped solids from excavated surfaces to insure adequate bonding compound thickness in the bonding interface, said shaped solid forming a smooth, continuous exterior.

2. An apparatus as recited in claim 1, comprising a kit of at least one insert with a mesial descender extending from said occlusal surface;

said mesial descender having a proximal surface, a facial descender surface for bonding, a lingual descender surface for bonding, a gingival surface for bonding and an axial surface for bonding.

3. An apparatus as recited in claim 1, comprising a kit of at least one insert having a distal descender extending from said occlusal surface;

said distal descender having a proximal surface, a facial descender surface for bonding, a lingual descender surface for bonding, a gingival surface for bonding and an axial surface for bonding.

4. An apparatus as recited in claim 1, comprising at least one insert having a mesial descender and a distal descender, said mesial descender extending from said occlusal surface toward the mesiogingival margin, and said distal descender extending from said occlusal surface toward the distogingival margin;

said mesial descender having a proximal surface, a facial descender surface for bonding, a lingual descender surface for bonding, a mesiogingival surface for bonding and an mesioaxial surface for bonding; and said distal descender having a proximal surface, a distofacial descender surface for bonding, a distolingual descender surface for bonding, a distogingival surface for bonding and a distoaxial surface for bonding.

5. An apparatus as recited in claim 1, comprising conical surface bumps on said pulpal floor, bonding surface of said shaped solids to properly space said shaped solids from excavated surfaces, to insure adequate bonding compound thickness in the bonding interface.

* * * * *